United States Patent
Calanchi et al.

(10) Patent No.: US 6,261,602 B1
(45) Date of Patent: Jul. 17, 2001

(54) PHARMACEUTICAL COMPOSITION FOR RAPID SUSPENSION IN AQUEOUS MEDIA

(75) Inventors: Massimo Maria Calanchi; Marco Giuseppe Raffaele Marconi; Luigi Giovanni Mapelli, all of Milan (IT)

(73) Assignee: Eurand International S.p.A. (IT)

( * ) Notice: Subject to any disclaimer, the term of this patent is extended or adjusted under 35 U.S.C. 154(b) by 0 days.

(21) Appl. No.: 09/297,213

(22) PCT Filed: Oct. 23, 1997

(86) PCT No.: PCT/EP97/05863

§ 371 Date: Sep. 21, 1999

§ 102(e) Date: Sep. 21, 1999

(87) PCT Pub. No.: WO98/17250

PCT Pub. Date: Apr. 30, 1998

(30) Foreign Application Priority Data

Oct. 23, 1996 (GB) ................................. 9622090

(51) Int. Cl.⁷ ............................. A61K 9/14; A61K 9/16; A61K 9/64; A61K 9/20
(52) U.S. Cl. ...................... 424/489; 424/490; 424/493; 424/496; 424/497; 424/456; 424/464
(58) Field of Search ................................... 424/489, 490, 424/493, 496, 497, 456, 464

(56) References Cited

U.S. PATENT DOCUMENTS 5,008,117 * 4/1991 Calanchi et al. ...................... 424/494
5,472,704 * 12/1995 Santus et al. ......................... 424/435

* cited by examiner

*Primary Examiner*—Thurman K. Page
*Assistant Examiner*—S. Tran
(74) *Attorney, Agent, or Firm*—Thompson Hine LLP

(57) ABSTRACT

The invention provides a granular product useful as a pharmaceutical carrier which can be used for the preparation of pharmaceutical compositions that are capable of rapid suspension in water or aqueous media including saliva. The compositions may be used by addition to a glass of water with stirring or taken directly in the mouth. The granular product may be prepared by a process which comprises subjecting a mixture of a thickening agent and a disintegrating agent to wet granulation with an aqueous medium as wetting agent or dry granulation and preparing the pharmaceutical composition from the granular product and the pharmaceutically active ingredient. A water-soluble inert excipient, which may be a sugar, may be mixed with the granular product prior to mixing with the pharmaceutically active ingredient.

16 Claims, No Drawings

PHARMACEUTICAL COMPOSITION FOR RAPID SUSPENSION IN AQUEOUS MEDIA

This application is a 371 of PCT/EP97/05863 filed Oct. 23, 1997.

The present invention relates to a process for the preparation of a pharmaceutical formulation suitable for the administration of drugs and in particular of microcapsules of drugs in a monodose sachet form, the contents of which form a rapid suspension in water or an aqueous medium, for instance, saliva in the mouth.

In the description and the claims which follow we will use mostly the terms microcapsules or microcapsulated drugs, but the present invention can also be applied to solid drugs particles (powders, crystals, granules) which are insoluble or slightly soluble in water or drinkable aqueous liquids (milk, fruit juices, etc.) and of which one desires to obtain an extemporary and homogeneous suspension.

In the following description and claims the term:
"microcapsule" is used to indicate drug particles, powders, crystals, granules, pellets and also liquid drops, coated in a polymeric membrane.

"microencapsulation" is generically the process used for the application of a membrane.

"pack or monodose sachet" is a container which contains a single dose of drug plus the excipients of the formulation.

"thickening or suspending substances" are substances which dissolve in water and which increase in density and viscosity allowing solid particles to be suspended.

Microencapsulation is a process known from some time and consists of coating substances with a continuous film based on natural or synthetic polymers.

The processes of microencapsulation are numerous. Many of these and the relative patents are cited and described in the volumes "Microcapsules and microencapsulation Techniques"(published in 1976) and "Microcapsules and other Capsules. Advance since 1975"(published in 1979) both by M. H. Guttcho. Among the preferred processes are those described in the U.S. Pat. Nos. 3,196,827 and 3,253,944 by D. E. Wurster which described methods of mechanical coating consisting of spraying a membrane around particles using suitable apparatus, and those cited in U.S. Pat. Nos. 3,415,758, 3,155,590 and 3,341,416 which described methods of chemicophysical coating based on the coacervation or separation of phases, in which polymer making up the membrane is dissolved in a suitable solvent or vehicle of microencapsulation and the substance to be dissolved is suspended in this solution and kept in agitation.

The coacervation of the polymer around the substance to be coated is obtained in various manners, such as for example temperature variation, addition of another more soluble polymer in the vehicle, addition of a non solvent of the polymer constituting the membrane, etc. The membrane can be hardened and so the microcapsules are separated from the vehicle for example by filtration or centrifuging and finally drying.

In the pharmaceutical field, microencapsulation is used to mask unpleasant tastes, for slowing down the release of the drug, for preventing irritation arising from contact of the drugs with the gastrointestinal mucosa, for protecting drugs from degradation, for separating drugs which react with each other, for transforming the drug into a more easily used form, such as for example, converting it from a liquid state into a powder composed of microcapsules.

A common form of dosage for the oral administration of drugs, and especially of microencapsulation drugs, is that of monodose sachets. This moreover is the most convenient solution, if not the only one, if one must administer high doses of drugs. Monodose sachets containing microcapsules have been prepared in the past, sometimes also on an industrial scale, as cited in the volume "Microencapsulation" by J. R. Nixon, Chapter 7, page 93.

However, they often present various disadvantages due especially to the hydrorepulsion of polymers making up the microcapsule membrane (for example polymers with a base of cellulose or waxy substances) and to the specific weight of the microencapsulated substances and therefore of the said microcapsules.

In fact when the contents of the sachets were poured out, as usual, in a glass of water or in fruit juice or in milk, the microcapsules formed a sediment on the bottom of the glass or floated on the surface, adhering partly to the walls of the said glass. This brought a notable inaccuracy to the quantity of the drug taken as well as poor acceptance by the patient who saw the particles floating or felt unpleasant scraping sensation in the mouth or throat when swallowing the contents at the bottom of the glass where the mass of sedimented particles was found.

The addition of thickening substances would delay and maybe also eliminate the separation of the nicrocapsules, but in practice has given negative results because these substances tend to form lumps on contact with water which dissolve slowly and only by resorting to vigorous mechanical agitation. It was attempted to disperse these thickening substances together with other components of the formula by mixing them in the usual powder mixers. Also with this method the formation of lumps could not be avoided, but was only partly reduced.

The above mentioned difficulties were mainly solved by the invention described in Italian patent no. 1183574 which refers to a formulation, and a method for obtaining it, characterised in that:

1) a thickening agent is micronized;
2) the thickening agent is suspended in an organic solution also containing a binding agent;
3) this suspension is applied by spraying it on to the surface of a substance which is easily soluble in water (sugar, sorbitol); and
4) the product obtaining is dried and once mixed with the microcapsules and the flavouring is used for filling the monodose sachets.

When the contents of the sachets are poured in water and agitated, as described in the examples of the patents cited, in about 1 minute a homogeneous microcapsule suspension is obtained.

In practice however it is seen that the patients, after having poured the sachet contents into water, do not stir with a spoon for at least 60 seconds, but stop after 20–30 seconds at the most. After this time the thickener is still not sufficiently dissolved and so a homogeneous suspension is not obtained and the previously cited difficulties are only partially eliminated.

WO 92/00731 discloses a system which reduces the mixing times. It was found that if an acid and a base substance are added, the thickening of the liquid and the homogeneous suspension of the microcapules is generally obtained by mixing for only 15–20 seconds. The solid pharmaceutical composition for addition to water to produce a suspension of a drug comprises:

a) a drug which is substantially water-insoluble or microencapsuled;
b) a thickening or suspending agent;

c) a pharmaceutically acceptable acid;
d) a pharmaceutically acceptable carbonate or bicarbonate. The weight ratio of c+d:b is from 1:1.5 to 1:15 and the amount of c+d is sufficient to obtain rapid hydration of the thickening or suspending agent b) when the composition is mixed with water such that a homogeneous suspension of the drug is obtained with 30 seconds. WO 92/00731 states that it is necessary that the acid and base substances, are very thoroughly mixed with the thickening substance and therefore they must be soluble, or suspended in the form of micronized powder, in the organic solvent used for applying of the suspension containing the thickener.

The process disclosed in WO 92/00731 has the disadvantage of using an organic solvent which may cause a problem as a result of flammability or pollution. The process also has the disadvantage of being an manufacturing method with the disadvantage of a low concentration of thickening agent. In consequence, in order to reach a viscosity suitable for maintaining the microcapsules in a homogeneous suspension, monodose sachets had to be filled with a large amount of ingredients which also caused high costs.

The present invention provides a novel pharmaceutically useful carrier for a water-insoluble or microencapsulated drug. The pharmaceutical compositions containing the carrier and the drug are capable of being dispersed rapidly when added to water or an aqueous medium, for example, when poured into water with stirring. The dispersion may take place quickly, for example, generally within a period of 30 seconds, preferably within a period of 20 seconds. The invention is associated with a number of advantages. One advantage is that the invention may be carried out in a manner that avoids lump formation when the pharmaceutical composition is added to water with stirring. A second advantage is that there is no need to use an organic solvent in the preparation of the pharmaceutical composition. A third advantage is that the pharmaceutical compositions may be prepared in a simple manner. A fourth advantage is that the invention may be carried out relatively cheaply because it permits a high concentration of thickening agent. The thickening agent is responsible for giving a viscosity sufficient to obtain a homogeneous aqueous suspension of the microcapsules. Because of the high content of thickening agent one may be able to achieve similar dispersion results to prior art compositions with only ½ or ⅓ of the suspending granulate. Hence the invention enables the pharmaceutical compositions to be prepared more cheaply.

The present invention provides a granulate composition useful as a pharmaceutically acceptable carrier. The carrier can be used to prepare water-suspendible pharmaceutical compositions. The granulate composition comprises one or more thickening agents and one or more disintegrating agents. The granulate composition is adapted to enable pharmaceutical compositions to be converted into homogeneous aqueous suspensions generally within a short period, preferably within 30 seconds, advantageously within 20 seconds, when the pharmaceutical compositions are added to water with agitation, preferably by stirring with a spoon. The pharmaceutical compositions may also be taken directly in the mouth where they give rise to a suspension of the drug in saliva as aqueous environment.

The granulate composition comprises one or more thickening agents and one or more disintegrating agents. The thickening agent is as defined above in respect of "thickening or suspending substance". It dissolves in the water and increases the viscosity of the aqueous medium when the pharmaceutical composition is dispersed in water. As examples of thickening agents there may be mentioned xanthan gum, carrageenan, alginates, agar-agar, tragacanth gum, guar gum, carruba gum, karaya gum or modified corn starch. The number of thickening agents chosen for use in the granulate composition is not critical. A single thickening agent may be chosen.

The granulate composition of the invention also includes one or more disintegrating agents. Disintegrating agents are excipients generally characterised either by a highly cross linked internal structure and a great affinity for water. They have the purpose of influencing the water uptake and the disintegration time of the pharmaceutical formulation in which they arc included. The disintegrating agent preferably operates by driving water into the granulate composition of the invention so as to cause the granulate to swell and burst apart. Thus, in the aqueous medium they operate as dispersing agents that allow the separation of the particle of thickening agent which can rapidly hydrate and dissolve without forming lumps. The optimal action of the disintegrating agent in achieving separation of the particles of the thickening agent can be obtained and controlled by adjusting the grade and/or the amount of the disintegrating agent. Although it is possible to use a single disintegrating agent, we prefer to use two or more such agents, advantageously two or three disintegrating agents.

As examples of disintegrating agents there may be mentioned alginic acid, carboxymethylcellulose calcium salt, colloidal silicon dioxide, magnesium aluminium silicate, starch and starch derivatives and sodium alginate, sodium starch glycolate, polyvinylpyrrolidone CL (cross-linked) and sodium carboxymethylcellulose CL (crosslinked).

We recommend that the ratio of the thickening agent or agents to the disintegrating agent or agents be within the range of 5 to 65 parts by weight, preferably 15 to 55 parts by weight, of thickening agents(s) to 95 to 35 parts by weight, preferably 85 to 45 parts by weight, of disintegrating agent(s). The granulate composition of the invention may consist exclusively of the disintegrating agent(s) and thickening agents. However, it may also contain minor amounts, for example, 0 to 30% by weight, preferably 0 to 20% by weight, of other components. As examples of such other components, there may be mentioned binders, fillers, lubricants, glidents, pharmaceutically acceptable acids, bases or buffers.

We recommend that the granulate composition of the invention comprising one of more thickening agents and one or more disintegrating agents has particle sizes within the range of 200 to 850 $\mu$m, preferably 250 to 750 $\mu$m. A particle size distribution higher than 850 $\mu$m may prolong the time necessary to obtain a viscosity sufficient to keep the microcapsules in suspension. On the other hand a case granulate having a particle size destribution lower than 200 $\mu$m can lead to lump formation.

The following compounds illustrate the substances that may be used as active pharmaceutical agents in pharmaceutical compositions of the invention:

| | |
|---|---|
| Acetylcisteine | Flucloxacillin |
| Acetylsalicylisc Acid | Glafenine |
| Amitriptyline | Gemfibrozil |
| Nicardipine | Guaifenesin |
| Bromazepam | Phenylpropanolamine |
| Fluoxetine | Ibuprofen |
| Cefalexin | Amitriptyline |

-continued

| | |
|---|---|
| Lithium Carbonate | Isosorbide mononitrate |
| Cephalosporins | Etodolac |
| Codeine Phosphate | Isosorbide dinitrate |
| Caffeine | Morphine |
| 5-aminosalicylic acid | Alkali metal halides |
| Dextro Methorphan | Ketoprofen |
| Diazepam | Metoclopramide |
| Penicillins | Paracetamol |
| Diclofenac | Ranitidine |
| Pancreatin | Prazosin |
| Diltiazem | Procainamide |
| Captopril | Amoxicillin |
| Dipyridamole | Pseudoephedrine |
| Carboxymethylcystein | Ambroxol |
| Erythromycin | Timus extract |
| Etofibrate | Verapamil |
| Furosemide | Vitamins |
| Cimetidine | Theophylline |

The present invention also provides a process for the preparation of the aforesaid granulate composition which comprises subjecting one or more thickening agents and one or more disintegrating agents to wet granulation with an aqueous medium as wetting agent or dry granulation. The granulate product may then be sieved to conform with the desired particle size distribution. The granulate product obtainable in this way is called the "base granulate".

The base granulate product may be mixed with a water-soluble inert excipient, for example, anhydrous sorbitol, mannitol, sucrose, lactose, fructose, maltodextrine, alanine or pentacrythrite to provide the product with bulk. The excipient preferably has sweetening properties. The ratio by weight of the inert excipient to the base granulate is preferably within the range of 0.3 to 5.0, advantageously 1.0 to 4.0.

The term "suspending granulate" will be used herein to refer to the product of mixing the base granulate with a water-soluble inert excipient or to refer to the base granulate product where the base granulate product is to be combined with the active ingredients to make pharmaceutical compositions.

The granulate products of the invention are homogeneously mixed with a pharmaceutically useful substance to prepare pharmaceutical compositions. The pharmaceutically useful substance is a product that is essentially water-insoluble or is coated with a water-insoluble coating or is microencapsulated.

Some materials for making the membranes of microcapsules are selectively water-insoluble at one pH range and water-soluble at another pH range. The granulate compositions of the invention and the pharmaceutical compositions of the invention may therefore include a pH-controlling agent to prevent premature dissolution of the membrane. For instance Eudragit L is a membrane that dissolves at pH 5–6 but does not dissolve at lower pH values. Citric acid is an example of a pH-controlling agent. It may be incorporated in the products of the invention to prevent premature dissolution of the membrane by reducing the pH in the mouth to about 4.

Once the pharmaceutical compositions of the invention have been obtained, the product is preferably divided up into single doses. The individual doses are preferably packaged separately, for example by enclosing each dose in a monodose sachet. The recommended concentration of the active pharmaceutical substance (including the coating or microcapsulating substance, where present) in the overall pharmaceutical composition is preferably within the range of 5% to 50%, advntageously 8% to 32%, on a weight/weight basis.

The pharmaceutical compositions of the invention are intended for use by suspension in water or an aqueous medium. They can be developed either as formulations to be poured directly into a glass of water, for instance, the formulations defined in the examples as "monodose sachets", or as formulations to be used by taking them directly in the mouth, for instance, formulations defined in the examples as "dry sachets".

The following flow sheet illustrates the manufacturing process of the invention:

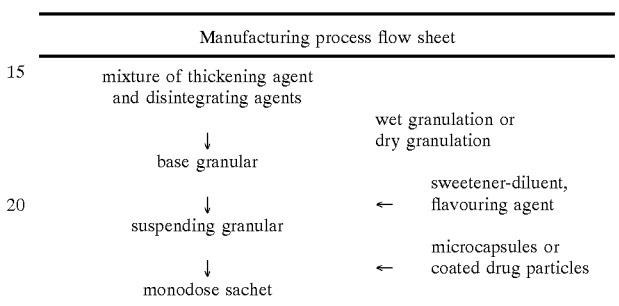

The invention will be illustrated by the following Examples. Trade marks have been used to give the names of the main ingredients in the Examples.

The chemical names and functions are given below:

| Chemical Name | Trade Mark | Function |
|---|---|---|
| Xanthan gum | Keltrol" | thickening agent |
| Carrageenan | Gelcarin" | thickening agent |
| Sodiumcarboxymethylcellulose CL (cross-linked) | Ac-di-Sol" | disintegrating agent |
| Cellulose microcrystalline | Avicel" | disintegrating agent |
| Polyvinylpyrrolidone CL (cross-linked) | Kollidon" | disintegrating agent |
| Sodium starch glycolate | Explotab" | disintegrating agent |
| Sorbitol | Karion" | sweetener-diluent |

The base granular is made by wet granulation in the case of Examples 1 to 4 and by dry granulation in the case of Examples 5 to 8.

EXAMPLE 1

(A) Preparation of the Base Granular 600 g of Keltrol F with particle size less than 150 μm, 300 g of Ac-di-Sol, 300 g of Avicel PH 200 and 600 g of Explotab were mixed in a cube mixer. This mixture was loaded into a fluid bed equipped with a rotor insert.

A granulate was obtained by spraying, at room temperature, on this mixture, 1000 g of an aqueous solution of citric acid (20% w/w).

Finally the product was dried at 40° C. and sieved to give a particle size distribution between 250 μm and 850 μm.

(B) Preparation of the Suspending Granular 1000 g of (A), with particle size distribution between 210 and 850 mm, were homogeneously mixed with 1875 g of Karion 10 g of Aspartame and 100 g of orange flavour.

Preparation of the Monodose Sachets 2985 g of (B) were homogeneously mixed with 1430 g of 5-aminosalicylic acid granules coated with Eudragit S and having a potency of 835 mg/g. The mixture was divided in sachets each having a weight of 4.437 g and a dosage of 1.2 g.

| Ingredients | | | Quantity (mg/sachet) |
|---|---|---|---|
| 5-aminosalicylic acid coated with Eudragit S | | | 1437.2 |
| Keltrol F | ⎫ | ⎫ | 301.5 |
| Ac-di-Sol | ⎪ | ⎪ | 150.7 |
| Avicel PH200 | ⎬ base granulate | ⎪ | 150.7 |
| Explotab | ⎪ | ⎪ | 301.5 |
| Citric acid | ⎭ | ⎬ suspending granulate | 100.5 |
| Karion | | ⎪ | 1884.4 |
| Aspartame | | ⎪ | 10.1 |
| Flavouring agent | | ⎭ | 100.5 |
| Total | | | 4437.1 |

The relatively high weight of each sachet is due to the fact that an unusually large amount of coated drug had to be suspended.

EXAMPLE 2

(A) Preparation of the Base Granular

Following the process described in the example 1, a granular (1000 g) composed of 300 g of Keltrol F, 300 g of Ac-di-Sol, 300 g of Kollidon CL and 100 g of citric acid, was prepared.

(B) Preparation of the Suspending Granular 1000 g of (A) were mixed, with 2000 g of Karion, 7.0 g of Aspartame and 75 g of orange flavour.

(C) Preparation of the Monodose Sachets 3082 g of (B), were homogeneously mixed with 339 g of Ibuprofen microcapsules having a cellulose acetate phthalate membrane and potency of 909.1 mg/g. The mixture was divided in sachets each having a weight of 2.220 g and a dosage of 200 mg.

| Ingredients | | | Quantity (mg/sachet) |
|---|---|---|---|
| Ibuprofen coated with cellulose acetate phthalate | | | 220.0 |
| Keltrol F | ⎫ | ⎫ | 194.7 |
| Ac-di-Sol | ⎪ | ⎪ | 194.7 |
| Kollidon CL | ⎬ base granular | ⎪ | 194.7 |
| Citric acid | ⎭ | ⎬ suspending granular | 64.9 |
| Karion | | ⎪ | 1297.8 |
| Aspartame | | ⎪ | 4.6 |
| Flavouring agent | | ⎭ | 48.6 |
| Total | | | 2220.0 |

EXAMPLE 3

(A) Preparation of the Base Granular

Following the process described in the example 1, a granular (1000 g) composed of 200 g of Keltrol F, 300 g of Ac-di-Sol, 250 g of Avicel PH 200, 150 g of Kollidon CL and 100 g of citric acid was prepared.

(B) Preparation of the Suspending Granular 1000 g of (A) were mixed with 2000 g of Karion, 7.0 g of Aspartame and 75 g of orange flavour.

(C) Preparation of the Monodose Sachets 3082 g of (B), were homogeneously mixed with 339 g of Ibuprofen microcapsules having a cellulose acetate phthalate membrane and potency of 909.1 mg/g. The mixture was divided in sachets each having a weight of 2.220 g and a dosage of 200 mg.

| Ingredients | | | Quantity (mg/sachet) |
|---|---|---|---|
| Ibuprofen coated with cellulose acetate phtalate | | | 220.0 |
| Keltrol F | ⎫ | ⎫ | 129.8 |
| Ac-di-Sol | ⎪ | ⎪ | 194.7 |
| Kollidon CL | ⎬ base granular | ⎪ | 97.3 |
| Avicel PH200 | ⎪ | ⎪ | 162.2 |
| Citric acid | ⎭ | ⎬ suspending granular | 64.9 |
| Karion | | ⎪ | 1297.9 |
| Aspartame | | ⎪ | 4.5 |
| Flavouring agent | | ⎭ | 48.7 |
| Total | | | 2220.0 |

EXAMPLE 4

(A) Preparation of the Base Granular

Following the process described in the example 1, a granular (1000 g) composed of 300 g of Keltrol F, 150 g of Avicel PH 200, 150 g of Ac-di-Sol, 300 g of Explotab, 100 g of citric acid was prepared.

(B) Preparation of the Suspending Granular 1000 g of (A) were mixed, with 1875 g of Karion, 10 g of Aspartame and 100 g of orange flavour.

(C) Preparation of the Monodose Sachets 2985 g of (B), were homogeneously mixed with 1124.9 g of coated pellets of Pancreatin, having an Eudragit L membrane and potency of 50.0 UI/mg. The mixture was divided in sachets each having a weight of 4.131 g and a dosage of 56530 UI.

The relatively high weight of the sachet is due to the unusually large amount of coated drug.

| Ingredients | | | Quantity (mg/sachet) |
|---|---|---|---|
| Pancreatin coated with Eudragit L | | | 1130.6 |
| Keltrol F | ⎫ | ⎫ | 301.5 |
| Ac-di-Sol | ⎪ | ⎪ | 150.7 |
| Avicel PH200 | ⎬ base granular | ⎪ | 150.7 |
| Explotab | ⎪ | ⎪ | 301.5 |
| Citric acid | ⎭ | ⎬ suspending granular | 100.5 |
| Karion | | ⎪ | 1884.9 |
| Aspartame | | ⎪ | 10.1 |
| Flavouring agent | | ⎭ | 100.5 |
| Total | | | 4131.0 |

The monodose sachets prepared in the preceding Examples were tested in the following procedure. The contents of one sachet of each Example were poured in a glass of water stirring with a teaspoon. The details and remarks are shown in the table I.

TABLE I

| Example No. | Base granular composition (%) | | Monodose sachet weight (g) | Water (ml) | Agitation (seconds) | Suspension characteristics |
|---|---|---|---|---|---|---|
| 1 | Keltrol | 30 | 4.437 | 100 | 20 | good |
| | Ac-di-Sol | 15 | | | | |
| | Avicel | 15 | | | | |
| | Explotab | 30 | | | | |
| | Citric acid. | 10 | | | | |

TABLE I-continued

| Example No. | Base granular composition (%) | | Monodose sachet weight (g) | Water (ml) | Agitation (seconds) | Suspension characteristics |
|---|---|---|---|---|---|---|
| 2 | Keltrol | 30 | 2.220 | 100 | 20 | fairly good |
|   | Ac-di-Sol | 30 | | | | |
|   | Kollidon | 30 | | | | |
|   | Citric acid | 10 | | | | |
| 3 | Keltrol | 20 | 2.220 | 100 | 20 | fairly good |
|   | Ac-di-Sol | 30 | | | | |
|   | Kollidon | 15 | | | | |
|   | Avicel | 25 | | | | |
|   | Citric acid. | 10 | | | | |
| 4 | Keltrol | 30 | 4.131 | 100 | 20 | good |
|   | Ac-di-Sol | 15 | | | | |
|   | Avicel | 15 | | | | |
|   | Explotab | 30 | | | | |
|   | Citric acid | 10 | | | | |

EXAMPLE 5

(A) Preparation of the Base Granular 333.4 g of Keltrol F with particle size less than 150 µm, 666.6 g of Avicel PH 200, 666.6 g of Explotab, 288.8 g of Ac-di-Sol, were mixed by means of a cube mixer. After the addition of 44.6 g of Magnesium Stearate as lubricant, the mixture was compressed into large tablets that were then crumbled and granulated with a 850 µm mesh. Finally the mixture was further mixed in a cube mixer.

(B) Preparation of the Suspending Granular 1000 g (A) with particle size distribution between 210 and 850 µm, were mixed in a cube mixer with 1300 g of Karion, previously sieved by 700 µm mesh.

(C) preparation of the Monodose Sachets

In a cube mixer, 2300 g of (B) were homogeneously mixed with 700 g of Theophylline microcapsules having an ethylcellulose membrane and potency of 900 mg/g. The mixture was divided in sachets each having a weight of 3.00 g and a dosage of 630 mg.

| Ingredients | | | Quantity (mg/sachet) |
|---|---|---|---|
| Theophylline coated with ethylcellulose | | | 700.0 |
| Keltrol F | base granular | suspending granular | 166.7 |
| Avicel PH200 | | | 333.3 |
| Ac-di-Sol | | | 144.4 |
| Explotab | | | 333.3 |
| Mg Stearate | | | 22.3 |
| Karion | | | 1300.0 |
| Total | | | 3000.0 |

EXAMPLE 6

(A) Preparation of the Base Granular

Following the process described in Example 5 a granular (1000 g) composed of 166.7 g of Keltrol F, 166.7 g of Karion, 1444.4 g of Ac-di-Sol, 333.3 g of Explotab, 166.7 g of Avicel PH 200,22.2 g of Mg Stearate, was prepared.

(B) Preparation of the Suspending Granular 1000 g (A), were mixed with 1670 g of Karion.

(C) Preparation of Monodose Sachets 2670 g of (B), were homogeneously mixed with 245 g of Cimetidine microcapsules having an ethylcellulose membrane and potency of 816.3 mg/g. The mixture was divided in sachets each having a weight of 2.915 g and a dosage of 200 mg.

| Ingredients | | | Quantity (mg/sachet) |
|---|---|---|---|
| Cimetidine coated with ethylcellulose | | | 245.0 |
| Keltrol F | base granular | suspending granular | 166.7 |
| Karion | | | 166.7 |
| Avicel PH200 | | | 166.7 |
| Ac-di-Sol | | | 144.4 |
| Explotab | | | 333.3 |
| Mg Stearate | | | 22.2 |
| Karion | | | 1670.0 |
| Total | | | 2915.0 |

EXAMPLE 7

(A) Preparation of Base Granular

Following the process described in Example 5, a granular (1000 g) composed of 166.7 g of Gelcarin, 333.3 g of Avicel PH 200,144,4 g of Ac-di-Sol, 333.3 g of Explotab, 22.2 g of Mg Stearate, was prepared.

(B) Preparation of the Suspending Granular 1000 g of (A), were mixed with 1670 g of Karion.

(C) Preparation of the Monodose Sachets 2670 g of (B), were homogeneously mixed with 330 g of Theophylline microcapsules having an ethylcellulose membrane and potency of 900.0 mg.g. The mixture was divided in sachets each having a weight of 3.00 g and a dosage of 297 mg.

| Ingredients | | | Quantity (mg/sachet) |
|---|---|---|---|
| Theophylline coated with ethylcellulose | | | 330.0 |
| Gelcarin | base granular | suspending granular | 166.7 |
| Avicel PH200 | | | 333.3 |
| Ac-di-Sol | | | 144.4 |
| Explotab | | | 333.3 |
| Mg Stearate | | | 22.3 |
| Karion | | | 1670.0 |
| Total | | | 3000.0 |

EXAMPLE 8

(A) Preparation of the Base Granular

Following the process described in Example 5, a granular (1000 g) composed of 300 g acid, 20 g of Mg Stearate, was prepared.

(B) Preparation of the Suspending Granular 1000 g of (A), were mixed with 1000 g of Karion.

(C) Preparation of the Monodose Sachet 2000 g of (B), were homogeneously mixed with 880 g of Ibuprofen having a cellulose acetate phtalate membrane and potency of 909.1 mg/g. The mixture was divided in sachets each having a weight of 2.880 g and a dosage of 800 mg.

| Ingredients | Quantity (mg/sachet) |
|---|---|
| Ibuprofen coated with cellulose acetate phtalate | 880.0 |

-continued

| Ingredients | | | Quantity (mg/sachet) |
|---|---|---|---|
| Keltrol F | base granular | suspending granular | 300.0 |
| Avicel PH200 | | | 150.0 |
| Ac-di-Sol | | | 130.0 |
| Explotab | | | 300.0 |
| Citric acid | | | 100.0 |
| Mg Stearate | | | 20.0 |
| Karion | | | 1000.0 |
| Total | | | 2880.0 |

The monodose sachets prepared in the preceding examples were tested in the following procedure. The content of each bag, was poured in a glass of water while stirring with a teaspoon. The details and remarks are shown in the table H.

TABLE II

| Example No. | Base granular composition (%) | | Monodose sachet weight (g) | Water (ml) | Agitation (seconds) | Suspension characteristics |
|---|---|---|---|---|---|---|
| 5 | Keltrol | 16.7 | 3.000 | 50 | 20 | good |
|  | Ac-di-Sol | 14.4 | | | | |
|  | Avicel | 33.3 | | | | |
|  | Explotab | 33.3 | | | | |
|  | Mg Stear. | 2.3 | | | | |
| 6 | Keltrol | 16.7 | 2.915 | 50 | 20 | good |
|  | Karion | 16.7 | | | | |
|  | Avicel | 16.7 | | | | |
|  | Ac-di-Sol | 14.4 | | | | |
|  | Explotab | 33.3 | | | | |
|  | Mg Stear. | 2.3 | | | | |
| 7 | Gelcarin | 16.7 | 3.000 | 50 | 20 | good |
|  | Ac-di-Sol | 14.4 | | | | |
|  | Explotab | 33.3 | | | | |
|  | Avicel | 33.3 | | | | |
|  | Mg Stear. | 2.3 | | | | |
| 8 | Keltrol | 30.0 | 2.880 | 50 | 30 | fairly good |
|  | Ac-di-Sol | 13.0 | | | | |
|  | Avicel | 15.0 | | | | |
|  | Explotab | 30.0 | | | | |
|  | Citric acid | 10.0 | | | | |
|  | Mg Stear. | 2.0 | | | | |

The above examples disclose the obtaining of a base granulate product in which the concentration of thickening agent ranges between 16.7% and 30%. In contrast the examples of WO 86/06626 and WO 92100731 show granulate products having a lower content of thickening agent, namely, ranging between 3.8 to 12.5%.

The ability of the aqueous vehicle for keeping the active ingredient in aqueous suspension depends upon the viscosity which in turn depends upon the amount of thickening agent used. Thus, generally speaking, the higher the content of the thickening agent in the base granulate product, the smaller is the amount of base granulate product needed per unit dose of active ingredient. As a result, the lower is the weight of an individual dose of the pharmaceutical composition of the invention. Hence the increased concentration of thickening agent in the case of the invention as mentioned in the previous paragraph is an advantage of the invention.

The following two examples concerning two different manufacturing processes to get Dry Sachet formulations.

EXAMPLE 9

Dry sachet formulation deriving from a base granulate made by wet granulation.

(A) Preparation of the Base Granulate

According to the process described in example 1, a granulate (1000 g) composed of 300 g of Keltrol F, 300 g of Ac-di-Sol, 300 g of Kollidon CL and 100 g of citirc acid was prepared.

(B) Preparation of the Suspending Granulate 1000 g of (A), were mixed with 4000 g of Karion, 4.0 g of Saccharine, 65 g of orange flavour, 45 g of Talc, 1.0 g of Syloid.

C) Preparation of the Dry Sachets 5115 g of (B) were homogeneously mixed with 1611 g of Ibuprofen microcapsules, having a cellulose acetate phthalate membrane and potency of 835.1 mg/g. The mixture was divided in sachets each having a weight of 1.000 g and a dosage of 200 g.

| Ingredients | | | Quantity (mg/sachet) |
|---|---|---|---|
| Ibuprofen coated with cellulose acetate phtalate | | | 880.0 |
| Keltrol F | base granulate | suspending granulate | 44.6 |
| Ac-di-Sol | | | 44.6 |
| Kollidon | | | 44.6 |
| Citric acid | | | 14.9 |
| Karion | | | 594.7 |
| Saccharine | | | 0.6 |
| Flavouring agent | | | 9.7 |
| Talc | | | 6.7 |
| Syloid | | | 0.1 |
| Total | | | 1000.0 |

EXAMPLE 10

Dry sachet formulation deriving from a base granulate made by dry granulation (A) Preparation of the Base Granulate of Keltrol F, 144 g of Ac-di-Sol, 333 g of Explotab and 23 g of Mg Stearate, was prepared.

(B) Preparation of the Suspending Granulate 1000 g of (A), were mixed with 2155 g of Karion, 2 g of saccharine, 37 g of orange flavour, 25 g of Talc.

C) Preparation of the Dry Sachets 3219 g of (B) were homogeneously mixed with 900 g of Ibuprofen microcapsules, having a cellulose acetate phthalate membrane and potency of 831.9 mg/g. The mixture was divided in sachets each having a weight of 1.100 g and a dosage of 200 g.

| .Ingredients | | | Quantity (mg/sachet) |
|---|---|---|---|
| Ibuprofen coated with cellulose acetate phtalate | | | 240.4 |
| Keltrol F | base granulate | suspending granulate | 44.6 |
| Ac-di-Sol | | | 38.5 |
| Avicel PH200 | | | 88.9 |
| Explotab | | | 88.9 |
| Mg Stearate | | | 88.9 |
| Karion | | | 575.6 |
| Saccharine | | | 0.5 |
| Flavouring agent | | | 9.8 |
| Talc | | | 6.7 |
| Total | | | 1100.0 |

What is claimed is:

1. A sachet dosage form prepared from a base granular product made by subjecting a mixture of one or more thickening agents and one or more disintegrating agents to wet granulation with an aqueous medium as wetting agent or to dry granulation, wherein said disentgrating agents are excipients characterized by either a highly cross liked internal structure or a great affinity for water.

2. The sachet dosage form as claimed in claim 1 wherein said mixture contains one thickening agent and two or more disintegrating agents.

3. The sachet dosage form as claimed in claim 1 having particle sizes within the range of about 200 µm to 850 µm.

4. The sachet dosage form as claimed in claim 3 having particle sizes within the range of about 200 µm to 750 µm.

5. The sachet dosage form as claimed in claim 1 containing at least one thickening agent selected from the group consisting of xanthan gum, carrageenan, alginates, agar-agar, tragacanth gum, guar gum, carruba gum, karaya gum and modified corn starch.

6. The sachet dosage form as claimed in claim 1 containing two or more disintegrating agents.

7. The sachet dosage form as claimed in claim 1 containing at least one disintegrating agent selected from the group consisting of alginic acid, carboxymethylcellulose calcium salt, colloidal silicon dioxide, magnesium aluminum silicate, starch and starch derivatives and sodium alginate, sodium starch glycolate, polyvinylpyrrolidone (cross-linked) and sodium carboxymethylcellulose (cross-linked).

8. The sachet dosage form as claimed in claim 1 containing about 5 to 65 parts by weight of thickening agent(s) per 95 to 35 parts by weight of disintegrating agent(s).

9. The sachet dosage form as claimed in claim 1 containing about 15 to 55 parts by weight of thickening agent(s) per 85 to 45 parts by weight of disintegrating agent(s).

10. The sachet dosage form as claimed in claim 1 containing up to about 30% by weight of at least one other component selected from the group consisting of binders, fillers, lubricants, glidents and pharmaceutically acceptable acids, bases and buffers.

11. A sachet dosage form useful in forming a suspension comprising a homogeneous mixture of the sachet dosage form of claim 1 and a water-soluble inert excipient.

12. The sachet dosage form of claim 11 wherein the excipient is a sweetening agent.

13. The sachet dosage form of claim 11 wherein the excipient is selected from the group consisting of anhydrous sorbitol, mannitol, sucrose, lactose, fructose, maltodextrine, alanine and pentacrythrite.

14. A sachet dosage form comprising:

the sachet dosage form of claim 1 or a suspension thereof; and a pharmaceutically active substance that is essentially water-insoluble, coated with a water-insoluble coating, or microencapsulated.

15. The sachet dosage form as claimed in claim 14 which forms a homogeneous aqueous suspension within about 20 seconds when a dose of said pharmaceutical composition is added to water and agitated.

16. The sachet dosage form as claimed in claim 14 containing at least one of the following pharmaceutically active substances:

| | |
|---|---|
| Acetylcisteine | Flucloxacillin |
| Acetylsalicylic Acid | Glafenine |
| Amitriptyline | Gemfibrozil |
| Nicardipine | Guaifenesin |
| Bromazepam | Phenylpropanolamine |
| Fluoxetine | Ibuprofen |
| Cefalexin | Amitriptyline |
| Lithium Carbonate | Isosorbide mononitrate |
| Cephalosporins | Etodolac |
| Codeine Phosphate | Isosorbide dinitrate |
| Caffeine | Morphine |
| 5-aminosalicylic acid | Alkali metal halides |
| Dextro Methorphan | Ketoprofen |
| Diazepam | Metoclopramide |
| Penicillins | Paracetamol |
| Diclofenac | Ranitidine |
| Pancreatin | Prazosin |
| Diltiazem | Procainamide |
| Captopril | Amoxicillin |
| Dipyridamole | Pseudoephedrine |
| Carboxymethylcystein | Ambroxol |
| Erythromycin | Timus extract |
| Etofibrate | Verapamil |
| Furosemide | Vitamins |
| Cimetidine | Theophylline. |

* * * * *

UNITED STATES PATENT AND TRADEMARK OFFICE
CERTIFICATE OF CORRECTION

PATENT NO. : 6,261,602 B1
DATED : July 17, 2001
INVENTOR(S) : Calanchi et al

It is certified that error appears in the above-identified patent and that said Letters Patent is hereby corrected as shown below:

Column 13, claim 1,
Line 6, the word "disentgrating" should be -- disintegrating --.
Line 7, the word "liked" should be -- linked --.

Signed and Sealed this

Eleventh Day of December, 2001

Attest:

NICHOLAS P. GODICI
Attesting Officer   Acting Director of the United States Patent and Trademark Office